United States Patent
Pasricha

(10) Patent No.: US 9,717,616 B2
(45) Date of Patent: Aug. 1, 2017

(54) METHODS AND DEVICES FOR TREATING OBESITY

(75) Inventor: Pankaj Jay Pasricha, Cupertino, CA (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 13/195,354

(22) Filed: Aug. 1, 2011

(65) Prior Publication Data

US 2012/0022322 A1 Jan. 26, 2012

Related U.S. Application Data

(62) Division of application No. 11/914,073, filed as application No. PCT/US2006/018344 on May 11, 2006, now abandoned.

(60) Provisional application No. 60/679,769, filed on May 11, 2005.

(51) Int. Cl.
  *A61F 2/04* (2013.01)
  *A61F 5/00* (2006.01)

(52) U.S. Cl.
  CPC ............ *A61F 5/003* (2013.01); *A61F 5/0003* (2013.01); *A61F 5/0069* (2013.01)

(58) Field of Classification Search
  CPC ............ A61B 18/18; A61B 19/00; A61F 2/04
  USPC ................... 623/23.64–23.68; 606/191–192; 424/422, 423, 489, 496, 497, 501; 600/30–31, 37
  See application file for complete search history.

(56) References Cited

U.S. PATENT DOCUMENTS

| | | | |
|---|---|---|---|
| 4,694,827 A | 9/1987 | Weiner et al. | |
| 5,259,399 A | 11/1993 | Brown | |
| 6,540,789 B1 | 4/2003 | Silverman et al. | |
| 6,579,301 B1 | 6/2003 | Bales et al. | |
| 6,660,301 B1 | 12/2003 | Vogel et al. | |
| 6,916,326 B2 | 7/2005 | Benchetrit | |
| 2003/0040804 A1* | 2/2003 | Stack et al. | 623/23.7 |
| 2003/0093117 A1 | 5/2003 | Saadat | |
| 2003/0153905 A1* | 8/2003 | Edwards et al. | 606/41 |

(Continued)

FOREIGN PATENT DOCUMENTS

WO  WO 93/19702  10/1993

OTHER PUBLICATIONS

Johnson, "Endoscopic therapy for GERD—baking, sewing, or stuffing: an evidence-based perspective," Reviews in Gastroenterological Disorders, 3:142-149,2003.

(Continued)

*Primary Examiner* — Yashita Sharma
(74) *Attorney, Agent, or Firm* — Norton Rose Fulbright US LLP

(57) ABSTRACT

Methods and devices for treating obesity. Pressure is applied to gastric walls in at least one segment of a stomach such that the pressure distends the gastric walls and induces satiety. A hollow capsule can be used to distend the gastric walls. Alternatively, a doughnut-shaped ring may be inflated to an amount sufficient to create intragastric tension and induce satiety. A c-ring including at least one balloon may be placed at a segment of the stomach, where the balloon inflates to a size that creates tension at the segment. A biocompatible material can be injected into the fundus and antrum of the stomach to stiffen the gastric wall to create a fullness feeling.

4 Claims, 3 Drawing Sheets

(56) References Cited

U.S. PATENT DOCUMENTS

| | | |
|---|---|---|
| 2004/0009224 A1 | 1/2004 | Miller |
| 2004/0037865 A1 | 2/2004 | Miller |
| 2004/0148034 A1 | 7/2004 | Kagan et al. |
| 2004/0247867 A1 | 12/2004 | Chaouk et al. |
| 2005/0096673 A1* | 5/2005 | Stack et al. .................. 606/151 |
| 2005/0245957 A1 | 11/2005 | Starkebaum et al. |

OTHER PUBLICATIONS

"Medtronic Introduces New Test for Acid Reflux," Medtronic, Inc., May 21, 2002.
"Clinical Trial for Gatekeeper Reflux Repair System," Medtronic, Inc .. , Nov. 18, 2003.
International Search Report, PCT/US2006/018344, Jun. 14, 2007.

\* cited by examiner

METHODS AND DEVICES FOR TREATING OBESITY

This application is a divisional of U.S. patent application Ser. No. 11/914,073 filed Jun. 25, 2008, which is a national phase application under 35 U.S.C. §371 of International Application No. PCT/US2006/018344 filed May 11, 2006, which claims priority to U.S. Provisional Patent Application, Ser. No. 60/679,769, which was filed May 11, 2005. The entire contents of each of the above-referenced disclosures is incorporated herein by reference in its entirety without disclaimer.

BACKGROUND OF THE INVENTION

1. Field of the Invention

The present invention relates generally to treating obesity. More particularly, the present invention provides techniques for stiffening the gastric walls and/or providing tension to the gastric wall to induce satiety, thereby treating obesity.

2. Description of Related Art

Obesity has become a global epidemic in recent years. In a National Health and Nutrition Examination Survey for 1999-2002 conducted by the Center for Disease Control and Prevention, it is estimated that approximately 30 percent of U.S. adults, or about 60 million people, ages 20 or higher, are obese, i.e., having a body mass index of 30 or higher. Approximately 65 percent of U.S. adults, ages 20 or higher, are overweight or obese, i.e., having a body mass index of 25 or higher. The same survey also found that 16 percent of children and adolescents between the ages of 6 and 19 are obese. The fact that the numbers are increasing as well as results of studies that show those who are overweight or obese are more likely to develop other health risks such as hypertension, dyslipidemia, diabetes, heart diseases, gallbladder diseases, strokes, respiratory problems, and even some cancers, have caused health officials to create a movement to help prevent and reduce obesity. As such, programs and regimens have been developed to curb these effects.

Aside from recommended daily physical activities, common weight reduction regimens include administration of systemic medications, which suppress the appetite or reduce the fat and/or sugar uptake of the digestive track. However, systemic medications often exhibit side effects, some of which may be severe.

Another commonly known treatment of obesity is gastric bypass surgery. The surgery divides the stomach into smaller portions and one section, known as the gastric pouch, is then connected to the small intestines. Due to the size of the pouch, food intake is limited, resulting in a reduction in calorie intake and weight loss. However, there are many complications associated with gastric bypass surgery. The surgery is highly invasive which can result in complications post surgery such as hernias, infections, gastritis, and sometimes death. Further, the surgery is irreversible, and thus, issues such as nutrient deficiencies can lead to other health problems such as anemia, osteoporosis, or other bone disorders.

Other alternatives for treating obesity include inserting intra-gastric devices such as gastric balloons into the stomach. Some of the devices may be secured to the stomach lining, while others, are free floating. However, the placement of these devices require large incisions and a lengthy recovery time. Additionally, these devices can deflate or can become detached from the lining and may migrate down the GI tract causing obstructions and necessitate removal.

Shortcomings mentioned above are not intended to be exhaustive, but rather are among many that tend to impair the effectiveness of previously known techniques for treating obesity; however, shortcomings mentioned here are sufficient to demonstrate that the methodologies appearing in the art have not been completely satisfactory and that a significant need exists for the techniques described and claimed in this disclosure.

SUMMARY OF THE INVENTION

Embodiments of the invention provide treatment for obesity by using the steady state of the intragastric pressure and wall tension in the stomach. The volume of the stomach can be decreased by changing the compliance of the stomach and thus, one may create gastric satiety.

Pressure may be applied to gastric walls in at least one segment of a stomach such that the pressure distends the gastric walls and induces satiety. A hollow capsule can be used to distend the gastric walls. Alternatively, a doughnut-shaped ring may be inflated to an amount sufficient to create intragastric tension and induce satiety. A c-ring including at least one balloon may be placed at a segment of the stomach, where the balloon inflates to a size that creates tension at the segment. A biocompatible material can be injected into the fundus and antrum of the stomach to stiffen the gastric wall to create a fullness feeling.

In one respect, the present invention provides a method for inducing gastric satiety. The method includes injecting a biocompatible material into spatially-separated first and second portions of an intragastric wall of the stomach (e.g., the fundus and antrum of the stomach) in an amount sufficient to stiffen the intragastric wall. The biocompatible material, which can be removed at later time, may include, but is not limited to, a hydrogel, collagen, fibrin, elastin, Teflon paste, a synthetic polymeric hydrogel, an inflatable hydrogel, a glycoaminoglycan, a proteoglycan, or microbeads suspended in a biological fluid lubricant.

In one respect, the invention involves a method for inducing gastric satiety. A biocompatible material is injected into spatially-separated first and second portions of an intragastric wall of a stomach in an amount sufficient to stiffen the intragastric wall for inducing satiety. The biocompatible material may be removable. The biocompatible material may include a hydrogel, collagen, fibrin, elastin, Teflon paste, a synthetic polymeric hydrogel, an inflatable hydrogel, a glycoaminoglycan, a proteoglycan, or microbeads suspended in a biological fluid lubricant. The first portion may include a fundus of the stomach and the second portion may include an antrum of the stomach.

In another respect, the invention involves a method for inducing gastric satiety, in which a hollow capsule is placed within a stomach wall for retention within the stomach. The hollow capsule is inflated to an amount sufficient to stiffen the wall for inducing satiety. The inflation may involve injecting fluid via an inlet of the hollow capsule. The method may also involve deflating the hollow capsule in an amount sufficient to induce satiety. The hollow capsule may be temporarily retained in the stomach for a period of at least one year. In other embodiments, retention periods may vary. For example, periods on the order of days, weeks, months, several years, or indefinitely are contemplated. Inflating may involve dynamically inflating according to one or more feedback loops.

In another respect, the invention involves a device for inducing gastric satiety, the device including a hollow capsule and an injector. The hollow capsule includes an inlet, and the capsule is configured to be placed and retained within a stomach wall. The injector is coupled to the inlet for adding fluid in an amount sufficient to stiffen the wall for inducing satiety. The device can also include a deflator for removing fluid from the hollow capsule.

In another respect, the invention involves a method for inducing gastric satiety, in which an inflatable ring is placed within a stomach for retention within the stomach. The volume of the inflatable ring is dynamically adjusted according to one or more feedback loops in an amount sufficient for inducing satiety. The step of dynamically adjusting the volume may involve injecting air or fluid into the inflatable ring. The ring may be temporarily retained in the stomach for a period of at least one year, although other shorter and longer time periods are contemplated. For example, the retention period may be on the order of days, weeks, months, several years, or indefinitely.

In another respect, the invention involves a device for inducing gastric satiety, the device including an inflatable ring and a regulatory device. The inflatable ring is configured to be placed and retained within a stomach. The regulatory device is coupled to the inflatable ring and is configured to dynamically adjust a volume of the inflatable ring according to one or more feedback loops in an amount sufficient for inducing satiety. The regulatory device may be positioned external to the stomach. The regulatory device may be or include a barostat.

In another respect, the invention involves a method for inducing gastric satiety, in which a ring including a balloon is attached to a stomach for retention within the stomach. The volume of the balloon is adjusted in an amount sufficient for exerting pressure on a wall of the stomach for inducing satiety. The step of adjusting a volume of the balloon may involve adjusting the volume of the balloon with a regulatory device in an amount sufficient for exerting pressure on the wall of the stomach. The step of attaching a ring may involve attaching the ring including a balloon to an antrum segment of the stomach. The ring may be temporarily retained in the stomach for a period of at least one year, although other shorter and longer time periods are contemplated. For example, the retention period may be on the order of days, weeks, months, several years, or indefinitely. The step of adjusting may involve dynamically adjusting according to one or more feedback loops.

In another respect, the invention involves a device for inducing satiety from within a stomach, the device including a ring, at least one balloon, and a regulatory device. The ring is configured to be coupled to a segment of the stomach and retained within the stomach. At least one balloon is coupled to the ring. The regulatory device is coupled to at least one balloon and is configured to adjust a volume of at least one balloon in an amount sufficient for exerting pressure on a wall of the stomach for inducing satiety. The device may also include a sensing device coupled to the balloon for monitoring a pressure associated with a wall of the stomach. The device may have two balloons coupled to the ring. The amount in which the volume is adjusted may be approximately a minimum therapeutic pressure. The regulatory device may be configured to adjust the volume of the balloon dynamically according to one or more feedback loops. The ring may be or include a c-shaped ring. The segment may include an antrum of the stomach.

The use of the word "a" or "an" when used in conjunction with the term "comprising" in the claims and/or the specification means "one or more," "at least one," and "one or more than one," unless explicitly noted otherwise. The term "coupled" is defined as connected, although not necessarily directly, and not necessarily mechanically.

The term "fluid" should be interpreted according to its ordinary meaning in the art, and should encompasses at least liquids and gases.

The term "satiety" or "inducing satiety" should be interpreted according to ordinary meanings in the art, and in a representative embodiment can be objectively measured or confirmed through an increase in baseline pressure associated with a stomach (e.g., a wall of the stomach). Such an increase in pressure can generate a feeling of fullness that can assist in appetite control and weight loss. In a representative and non-limiting embodiment, inducing satiety can involve an increase in a baseline pressure associated with the stomach in a range of about 8-14 mm Hg.

These, and other, embodiments of the invention will be better appreciated and understood when considered in conjunction with the following description and the accompanying drawings. It should be understood, however, that the following description, while indicating various embodiments of the invention and numerous specific details, is given by way of illustration and not of limitation. Many substitutions, modifications, additions and/or rearrangements may be made within the scope of the invention as defined in the claims, and the invention includes all such substitutions, modifications, additions and/or rearrangements.

BRIEF DESCRIPTION OF THE DRAWINGS

The following drawings form part of the present specification and are included to further demonstrate certain aspects of the present invention. The figures are examples only. They do not limit the scope of the invention.

DESCRIPTION OF ILLUSTRATIVE EMBODIMENTS

The stomach is responsible for handling and processing food for healthy and efficient digestion downstream. The proximal stomach serves to accommodate food initially and subsequently transfers it to the distal stomach where the food is ground down by the milling action of the antropyloric unit. The food is broken down into small, easily digestible particles that are allowed to enter the duodenum in a regulated manner. Excessive tension in either the proximal and/or distal stomach may induce dyspeptic symptoms as well as contribute to satiety. As such, increasing gastric wall tension and/or gastric wall stiffening to a critical level prior to or during ingestion of a meal may limit the intake of food due to the induced satiety from the tension. The level of tension needed to induce satiety may vary from subject to subject due to the wall tension being a function of both pressure and compliance.

In one embodiment, in order to reduce compliancy and increase stomach wall tension, a biocompatible material may be injected into the stomach, and particularly the stomach wall in a representative embodiment. The biocompatible material stiffens and/or increases the tension of the muscles of the wall and creates for the subject a feeling of fullness. The biocompatible material may be, for example, a hydrogel that is biodegradable over time or can be removed. As such, the process can be a non-permanent, reversible solution for treating obesity. Alternatively, the biocompatible material, which may be removable, may include, but is not limited to different forms of collagen, fibrin, elastin, Teflon paste, synthetic polymeric hydrogel, inflatable hydrogel, glycoaminoglycan, a proteoglycan, or microbeads suspended in a biological fluid lubricant.

Figure 1:
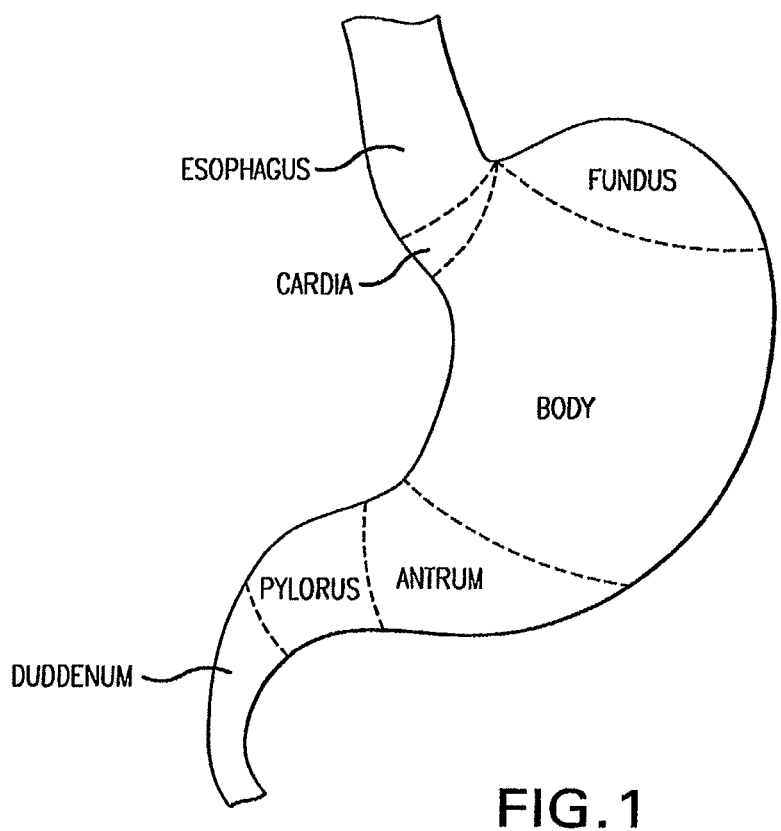
FIG. 1 shows a diagram of a stomach.

The injection of the biocompatible material, which may be an endoscopic (submucosal) injection, may be performed on the fundus and antrum of the stomach, e.g., a proximal and distal portion of the stomach, shown in FIG. 1. The increased tension and/or stiffening of the gastric walls in these two areas induces satiety, but does not block or obstruct the passage of food like prior methods of treating obesity.

Figure 2A:
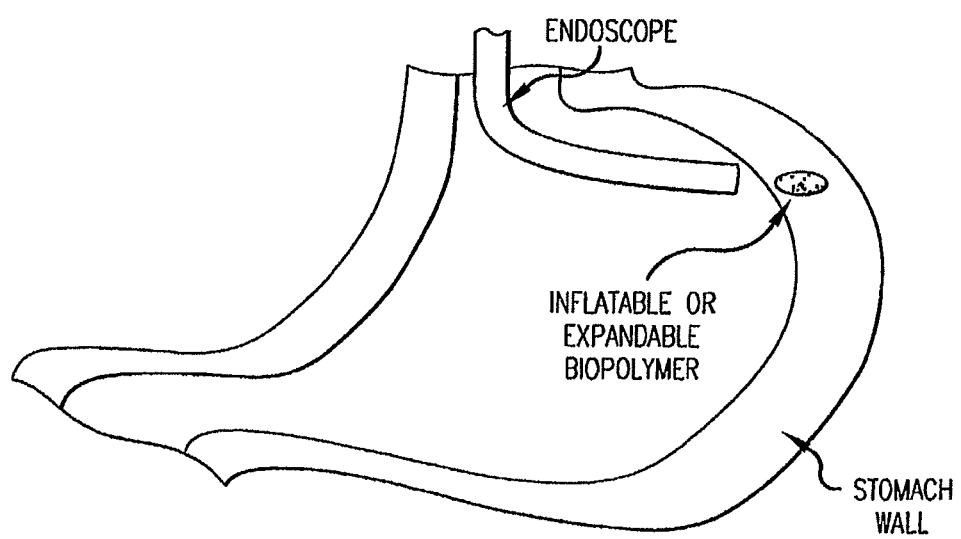
FIGS. 2A-2C show techniques for treating obesity, in accordance with embodiments of the invention.
Figure 2B:
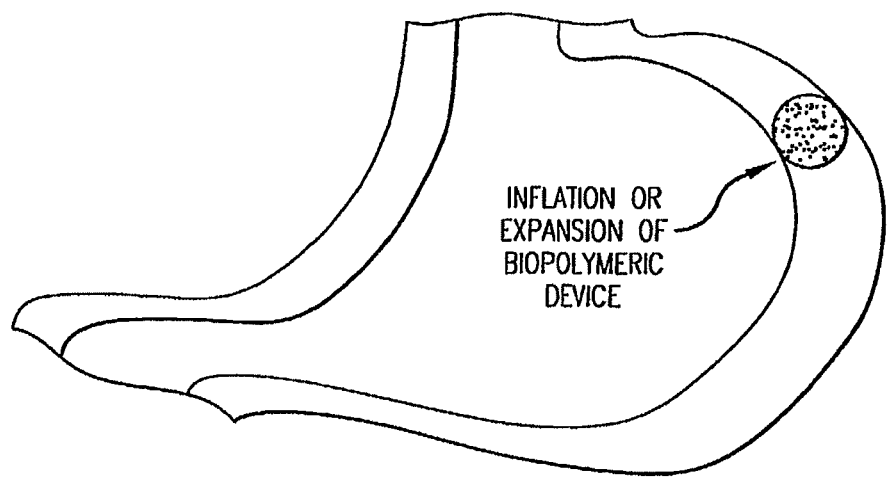

In other embodiments, a device may be used to increase the tension of gastric walls. The device may include a hollow capsule, which may be placed and retained within the stomach wall via a minimally invasive procedure such as endoscopic or percutaneous approaches, as seen in FIG. 2A. When the hollowed device is filled or inflated, the hollow capsule expands and distends the wall of the stomach causing stiffening of the gastric walls, as shown in FIG. 2B. In one embodiment, the hollow capsule may be inflated by a fluid, such as, but not limited to, an innocuous fluid. The innocuous fluid may be injected by an injector, e.g., an endoscopic needle, into an input port of the hollow capsule. The innocuous fluid may fill the hollow capsule to a point that induces satiety, which may vary from person to person. It is noted that any fluid may be used to fill the hollow capsule. Additionally, air, different forms of gels, or other materials may be used to fill the hollow capsule in an amount sufficient to create intragastric tension. The capsule may be retained within the stomach for various periods of time. In one embodiment, the capsule is retained indefinitely (e.g., until the natural death of a patient). In other embodiments, it may be retained temporarily (e.g., it may be removed at some time during the patient's lifetime), but for extended periods. For example, in different embodiment, the capsule may be retained for at least one week, two weeks, three weeks, four weeks, one month, two months, three months, four months, five months, six months, seven months, eight months, nine months, ten months, eleven months, one year, two years, three years, four years, five years, six years, seven years, eight years, nine years, ten years, twenty years, thirty years, forty years, fifty years, or any period in between.

Figure 2C:
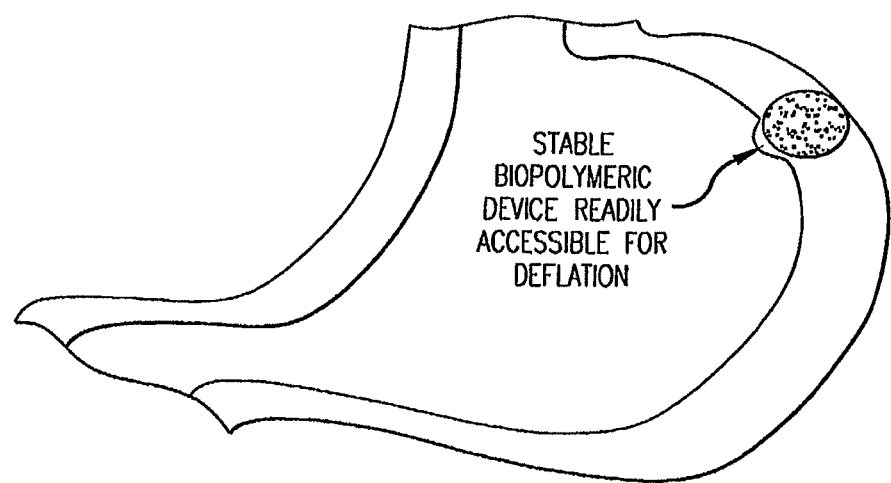

As noted above, the gastric tension needed to induce satiety may vary from person to person. Additionally, the gastric tension needed may change in an individual as dietary habits change. Thus, the hollow capsule may be tailored to adapt to one's needs. For example, the fluid or other material used to fill the hollow capsule may be removed as the effect on the person changes, as seen in FIG. 2C. Alternatively, multiple injections of the fluid or other materials into the hollow capsule may be performed as needed. In one embodiment, the patient may provide feedback about the proper amount of fluid or other material needed to induce satiety. For example, a first procedure may use amount X of fluid, and the patient may indicate that he or she generally does not feel satiated in response. An additional amount Y may then be added in one or more follow-up procedures until the patient achieves a feeling of satiety sufficient to assist in weight loss or change in eating habits. Likewise, if an initial procedure produces excessive pressure, adjustments may be made in some embodiments to reduce the pressure in one or more follow-up procedures. For example, fluid may be removed or even redistributed to achieve an effect satisfactory for satiety and ultimate weight loss.

Figure 3:
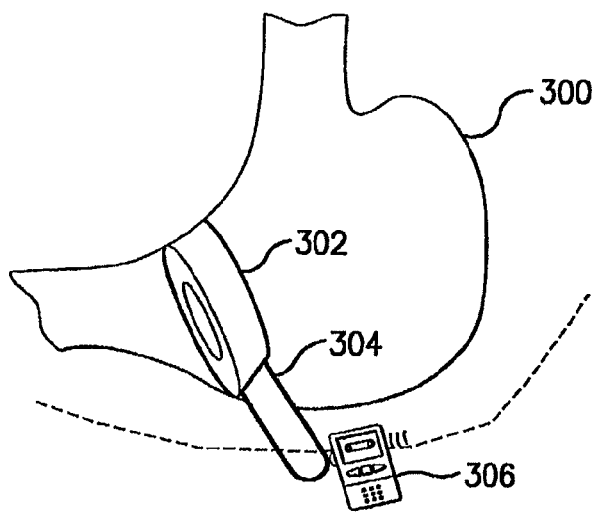
FIG. 3 shows a device for treating obesity, in accordance with embodiments of the invention.

In an alternative embodiment, ring 302 is placed, via a minimally invasive routine, such as endoscopic and/or percutaneous approaches, into stomach 300, as shown in FIG. 3. The ring may be retained within the stomach for various periods of time. In one embodiment, the ring is retained indefinitely (e.g., until the natural death of a patient). In other embodiments, it may be retained temporarily (e.g., it may be removed at some time during the patient's lifetime), but for extended periods. For example, in different embodiment, the ring may be retained for at least one week, two weeks, three weeks, four weeks, one month, two months, three months, four months, five months, six months, seven months, eight months, nine months, ten months, eleven months, one year, two years, three years, four years, five years, six years, seven years, eight years, nine years, ten years, twenty years, thirty years, forty years, fifty years, or any period in between.

Ring 302 may be an inflatable ring. Coupled to inlet/outlet port 304 of ring 302 is regulatory device 306, such as but not limited to, a barostat, which may be an external device or may be buried partially or completely subcutaneously. Regulatory device 306 may be adapted to sense the pressure and volume of ring 302 and adjust the pressure and volume such that a segment of stomach 300 is distended in a manner sufficient to create satiety. In one embodiment, regulatory device 306 may dynamically change the pressure and volume exerted by ring 300 in such a way to maintain a constant distending pressure. In more general embodiments, the dynamic nature of changing pressure or volume is done in response to one or more feedback loops. For example, based on one or more measurements (e.g., pressure, volume, temperature, etc.), a property of the ring may be modified (e.g., it may be inflated or deflated or even change position) in a way to affect at least one of those measurements. Measurements may then be retaken and an appropriate response generated. Through such a dynamic adjustment process, optimal conditions for inducing satiety may be achieved and consistently maintained. In one embodiment, at least one of the measurements may be patient-based or patient-dictated. For example, a patient may provide a signal indicating that he or she feels satiated, and that signal may be used in the dynamic adjustment process to maintain or store the physical conditions (e.g., pressure or volume) that achieve satiety for that specific patient.

Ring 300 may be an inflatable ring and the pressure and volume may be controlled by supplying to or removing from ring 300 fluids, air, or other material via inlet/outlet port 304 as determined by regulatory device 306.

Figure 4A:
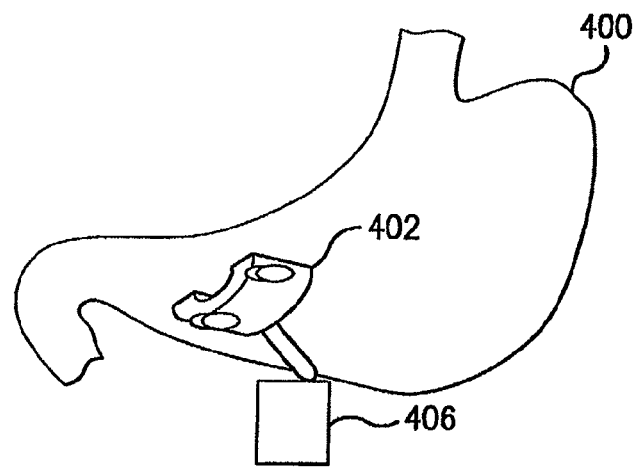
FIG. 4A shows a device for treating obesity, in accordance with embodiments of the invention.
Figure 4B:
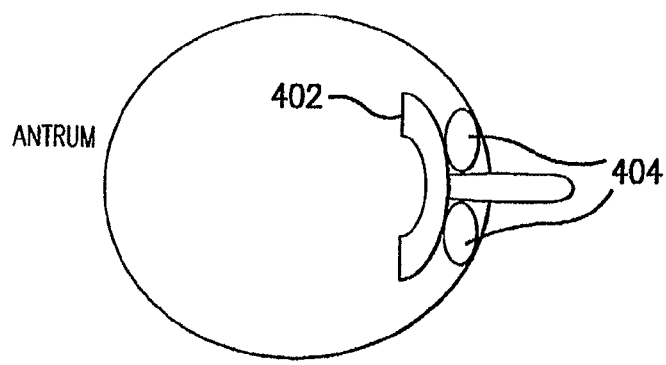
FIG. 4B shows a cross-section of the device for treating obesity in FIG. 4A, in accordance with embodiments of the invention.

For example, ring 302 may be placed in a compressed form into a subject and may be inflated via inlet/outlet port 304 by air, fluids, or other materials. As the pressure and volume of ring 302 increases, e.g., distending a portion of the stomach, the subject may feel an unpleasant sensation and/or satiety. The pressure and volume at which the unpleasant sensation and/or satiety occurs is called the minimum therapeutic pressure (MTP). Regulatory device 306 may then be set to maintain a baseline pressure and volume corresponding to the MTP in between meal intakes. Once the subject eats, normal physiology predicts that the stomach will expand, and the pressure and volume of ring 302 may decrease. A threshold value may be programmed into regulatory device 306 such that once the pressure and volume decreases, the device 306 will trigger an inflation of ring 302 until MTP is achieved. MTP allows for an induced satiety and an aversive response to further eating. In one embodiment, the pressure and volume of ring 302 may be maintained for a time period, e.g., 2 hours, before regulatory device 306 reverts back to the MTP. It is noted that different time periods may be used and may change based on the needs of the subject, and different feedback techniques can be used to achieve a degree of satiety suitable for weight loss In another embodiment, an exerting device, an example of which is shown in FIGS. 4A and 4B, may be used to apply pressure to a segment of a stomach to induce satiety. The device may be retained within the stomach for various periods of time. In one embodiment, the device is retained indefinitely (e.g., until the natural death of a patient). In other embodiments, it may be retained temporarily (e.g., it may be removed at some time during the patient's lifetime), but for extended periods. For example, in different embodiment, the device may be retained for at least one week, two weeks, three weeks, four weeks, one month, two months, three months, four months, five months, six months, seven months, eight months, nine months, ten months, eleven months, one year, two years, three years, four years, five years, six years, seven years, eight years, nine years, ten years, twenty years, thirty years, forty years, fifty years, or any period in between.

Unlike prior art methods, which are lumen occluding, ring 402 may be placed into stomach 400 at a specific portion, as shown in FIG. 4A. For example, ring 402 may be placed in the antrum segment of the stomach, where ring 402 provides for the distension of the stomach wall at the antrum, as shown in FIG. 4B. It is noted that ring 402 may be placed in different segments of the stomach, including but not limited to, the fundus, the cardia, or the pylorus segment of the stomach.

Ring 402, which may be in a c-shaped configuration, may be a scaffold or platform supporting one or more balloons 404. Balloon 404 may be inflated to an amount sufficient to exert pressure on the wall of stomach 400. For example, a regulatory device 406, coupled to the balloon 404 may sense the pressure and volume of the balloon. If the pressure and volume is below a threshold, i.e., the pressure on the wall of stomach 400 is insufficient for inducing satiety, balloon 404, connected via guides or remotely by radiofrequency, may be inflated. Alternatively, balloon 404 may include a sensing device (not shown) for monitoring the intragastric pressure. If the intragastric pressure is insufficient for inducing satiety, the sensing device may trigger an injector which may inflate the balloon 404 to a level where the pressure applied creates a fullness feeling for the subject.

The increase in pressure that can be used in embodiments described in this disclosure for inducing satiety may vary from patient to patient, and can be adjusted dynamically according to one or more feedback loops with or without input from the patient and, in representative embodiments, with the assistance of one or more monitors, sensors, or measurement devices. In one embodiment, an increase in baseline pressure of about 8-14 mm Hg (millimeters of Mercury) may be sufficient for inducing satiety. In other embodiments, inflation, fluid addition, fluid reduction, or the like that leads to a pressure elevation of about 1 mm Hg, 2 mm Hg, 3 mm Hg, 4 mm Hg, 5 mm Hg, 6 mm Hg, 7 mm Hg, 8 mm Hg, 9 mm Hg, 10 mm Hg, 11 mm Hg, 12 mm Hg, 13 mm Hg, 14 mm Hg, 15 mm Hg, 16 mm Hg, 17 mm Hg, 18 mm Hg, 19 mm Hg, 20 mm Hg, 21 mm Hg, 22 mm Hg, 23 mm Hg, 24 mm Hg, or 25 mm Hg may be sufficient for inducing satiety. Other pressure ranges may be between about 1-7, 2-8, 3-9, 4-10, 5-11, 6-12, 7-13, 9-15, 10-16, 11-17, 12-18, 13-19, 14-20, 15-21, 16-22, 17-23, 18-24, or 19-25 mm Hg. In still other embodiments, a different pressure value may be used that is suitable for inducing satiety in a given patient, and this value may be determined through interviewing the patient or through an appropriate feedback routine. For example, satiety for a given patient may be objectively determined through gathering of patient data associated with different pressure values—through appropriate patient feedback, an optimal or preferred pressure value for inducing satiety can be determined.

With the benefit of the present disclosure, those having skill in the art will comprehend that techniques claimed herein may be modified and applied to a number of additional, different applications, achieving the same or a similar result. For example, for each embodiment disclosed here, inflation or otherwise increasing pressure or volume of an inserted device may be done dynamically according to one or more feedback loops. A first procedure may use amount X of fluid, and the patient may indicate that he or she generally does not feel satiated in response. An additional amount Y may then be added in one or more follow-up procedures until the patient achieves a feeling of satiety sufficient to assist in weight loss or change in eating habits. Likewise, if an initial procedure produces excessive pressure, adjustments may be made in some embodiments to reduce the pressure in one or more follow-up procedures. For example, fluid may be removed or even redistributed to achieve an effect satisfactory for satiety and ultimate weight loss. The claims cover all such modifications that fall within the scope and spirit of this disclosure.

REFERENCES

Each of the following references is incorporated by reference in its entirety:
U.S. Patent Application No. 2003020388
U.S. Patent Application No. 20040037865
U.S. Pat. No. 5,259,399

The invention claimed is:

1. A device for inducing gastric satiety, comprising:
an inflatable, doughnut-shaped ring configured to be placed and retained within a stomach for a week or more and configured, once inflated, to be dynamically adjustable by a regulatory device in response to feedback provided by a feedback loop; and a regulatory device coupled to the inflatable ring and configured to dynamically adjust the volume of the inflatable ring, after inflation, in response to one or more feedback loops to distend the gastric wall to induce satiety.

2. The device of claim 1, where the regulatory device is positioned external to the stomach.

3. The device of claim 1, wherein the regulatory device comprises a barostat.

4. The device of claim 1, wherein the regulatory device is configured to receive patient feedback.

* * * * *